US00PP28705P3

(12) United States Plant Patent
Verschoor

(10) Patent No.: US PP28,705 P3
(45) Date of Patent: Nov. 28, 2017

(54) ***PHLOX* PLANT NAMED 'KAZI15789'**

(50) Latin Name: *Phlox drummondii*
Varietal Denomination: KAZI15789

(71) Applicant: Klemm+Sohn GmbH & Co. KG, Stuttgart (DE)

(72) Inventor: Katrin Verschoor, Klaaswaal (NL)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 9 days.

(21) Appl. No.: 14/999,171

(22) Filed: Apr. 6, 2016

(65) Prior Publication Data

US 2017/0295694 P1 Oct. 12, 2017

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Susan McCormick Ewoldt
(74) *Attorney, Agent, or Firm* — Barbara Campbell; Bethany R. Roahrig; Cochran Freund & Young, LLC

(57) ABSTRACT

A new *phlox* plant particularly distinguished by a compact, upright to outwardly spreading and mounding habit, and pink flowers, is disclosed.

1 Drawing Sheet

Genus and species: *Phlox drummondii.*
Variety denomination: 'KAZI15789'.

BACKGROUND OF THE NEW PLANT

The present invention comprises a new and distinct variety of *phlox*, botanically known as *Phlox drummondii* and hereinafter referred to by the variety name 'KAZI15789'. 'KAZI15789' originated from a breeding program in Mijnsheerenland, Netherlands in summer 2008 between unnamed and un-patented *phlox* plants. Seeds from the breeding program were obtained and plants were grown for evaluation.

A single plant was selected in June 2009 and subsequently named 'KAZI15789'. In July 2009, 'KAZI15789' was first vegetatively propagated by stem cuttings in Mijnsheerenland, Netherlands and in August 2009 in Stuttgart, Germany. 'KAZI15789' was found to reproduce true to type in successive generations of asexual propagation via stem cuttings in Mijnsheerenland, Netherlands and Stuttgart, Germany.

SUMMARY

The following are the most outstanding and distinguishing characteristics of this new variety when grown under normal horticultural practices in Stuttgart, Germany.

1. A compact, upright to outwardly spreading and mounding habit; and
2. Pink flowers.

DESCRIPTION OF THE PHOTOGRAPH

This new *phlox* plant is illustrated by the accompanying photograph which shows an overall view of the whole plant. The photograph is of an approximately 15-week-old plant grown in Stuttgart, Germany under greenhouse conditions in June 2012. The colors shown are as true as can be reasonably obtained by conventional photographic procedures.

DESCRIPTION OF THE NEW VARIETY

The following detailed descriptions set forth the distinctive characteristics of 'KAZI15789'. The data which define these characteristics were collected from asexual reproductions carried out in Stuttgart, Germany. Data was collected on 10-week-old plants after potting in the greenhouse in Stuttgart, Germany. Color references are to The R.H.S. Colour Chart of The Royal Horticultural Society of London (R.H.S.), 5$^{th}$ edition (2007).

Classification:
- *Family.*—Polemoniaceae.
- *Botanical.—Phlox drummondii.*
- *Designation.*—'KAZI15789'.

Propagation:
- *Type.*—Stem cuttings.
- *Time to initiate roots, summer.*—About five days at temperatures of about 20 degrees C.
- *Time to initiate roots, winter.*—About seven days at temperatures of about 20 degrees C.
- *Time to produce a rooted plant, summer.*—About three weeks at temperatures of about 20 degrees C.
- *Time to produce a rooted plant, winter.*—About four weeks at temperatures of about 20 degrees C.
- *Root description.*—Fine, fibrous, white in color.
- *Rooting habit.*—Freely branching, dense.

Plant:
- *Plant and growth habit.*—Compact, upright to outwardly spreading and mounding.
- *Plant height.*—13.5 cm.
- *Plant width (spread).*—16.0 cm.

Lateral branches or stems:
- *Length.*—12.0 cm.
- *Diameter.*—3.0 mm.
- *Internode length.*—2.0 cm.

*Strength*.—Strong.
*Texture*.—Pubescent.
*Color*.—RHS 145A.
*Anthocyanin*.—Absent.

Leaves:
*Arrangement*.—Opposite, simple.
*Length*.—3.7 cm.
*Width*.—1.2 cm.
*Shape*.—Elliptic.
*Apex*.—Apiculate (ending abruptly in a small distinct point).
*Base*.—Truncate to obtuse.
*Margin*.—Finely serrate.
*Texture* (*both upper and lower surfaces*).—Smooth, glabrous.
*Venation pattern*.—Pinnate.
*Color*.—Developing leaves: Upper surface: RHS 146A. Lower surface: RHS 147C. Fully expanded (mature) leaves: Upper surface: RHS 146A. Lower surface: RHS 147C. Venation: RHS 144B.
*Position of broadest part of leaf*.—At the middle.
*Leaf variegation*.—Absent.
*Anthocyanin coloration on upper surface*.—Absent.
*Undulation of margin*.—Absent or weak.

Petiole:
*Length*.—1.0 mm.
*Diameter*.—1.0 mm.
*Texture* (*both upper and lower surfaces*).—Smooth, glabrous.
*Color*.—Upper surface: RHS N144B. Lower surface: RHS 145C.

Flower:
*Flower type and flowering habit*.—Single rotate salverform flowers arranged in small panicles.
*Quantity of flowers per inflorescence*.—Freely flowering habit with about four flowers per inflorescence.
*Fragrance*.—Moderately fragrant, sweet, pleasant.
*Natural flowering season*.—Continuously flowering from summer to late summer in Germany.
*Postproduction longevity*.—Flowers last about three to four days on the plant, flowers not persistent.
*Flower buds*.—Height: 9.0 mm. Diameter: 3.0 mm. Shape: Narrowly obovate. Color: RHS 75D.
*Inflorescence height*.—3.1 cm.
*Inflorescence diameter*.—6.5 cm.
*Flower diameter*.—2.7 cm.
*Flower depth*.—1.4 cm.
*Flower throat diameter*.—3.0 mm.
*Flower tube length*.—1.3 cm.
*Flower tube diameter, at the base*.—1.5 mm.
*Perianth*.—Present, not achlamydeous.

Petals:
*Quantity per flower and arrangement*.—Five petals arranged in a single whorl and fused at the base into a narrow tube.
*Length from throat*.—1.0 cm.
*Width*.—1.2 cm.
*Shape*.—Spatulate.
*Apex*.—Rounded.
*Margin*.—Entire.
*Texture* (*both upper and lower surfaces*).—Smooth, glabrous.
*Texture of throat*.—Smooth, glabrous.
*Texture of tube*.—Smooth, glabrous.
*Color*.—Developing petals: Upper surface: RHS 75C. Lower surface: RHS 75D. Fully expanded petals: Upper surface: RHS 75C. Lower surface: RHS 75D. Flower throat: RHS 75B. Flower tube: RHS 69D.

Sepals:
*Quantity per flower and arrangement*.—5.
*Length*.—1.0 cm.
*Width*.—1.0 mm.
*Shape*.—Lanceolate.
*Apex*.—Narrowly apiculate.
*Margin*.—Entire.
*Texture* (*both upper and lower surfaces*).—Smooth, glabrous.
*Color*.—Upper surface: RHS 146B. Lower surface: RHS 146C.
*Anthocyanin coloration*.—Absent.

Peduncles:
*Length*.—2.0 cm.
*Diameter*.—3.0 mm.
*Angle*.—Upright.
*Strength*.—Strong.
*Texture*.—Smooth, glabrous.
*Color*.—RHS 145A.

Pedicels:
*Length*.—1.2 cm.
*Diameter*.—1.0 mm.
*Angle*.—30 degrees from the peduncle axis.
*Strength*.—Strong.
*Texture*.—Smooth, glabrous.
*Color*.—RHS 145A.
*Anthocyanin*.—Absent.

Reproductive organs:
*Stamens*.—Quantity per flower: 5. Filament length: 5.0 mm. Filament color: RHS 157B. Anther shape: Oblong. Anther length: 2.0 mm. Anther color: RHS 14A. Pollen amount: Abundant. Pollen color: RHS 14A.
*Pistils*.—Quantity per flower: 1. Pistil length: 4.0 mm. Stigma shape: Bi-parted. Stigma color: RHS 3B. Style length: 2.0 mm. Style color: RHS 149C. Ovary color: RHS 144A.

Fruit and seed set: Seeds and fruit development have not been observed.

Disease and pest/insect resistance: None observed.

COMPARISON WITH KNOWN VARIETY

'KAZI15789' can be compared to the commercial variety 'Phloxy Lady Pink' (patent status unknown). Differences between the two varieties are described in Table 1:

TABLE 1

Comparison with Similar Variety

| Trait | 'KAZI15789' | Commercial line 'Phloxy Lady Pink' |
|---|---|---|
| Habit | Compact, upright to outwardly spreading and mounding plant and growth habit | Strong, upright |

I claim:

1. A new and distinct variety of *phlox* plant named 'KAZI15789' as illustrated and described herein.

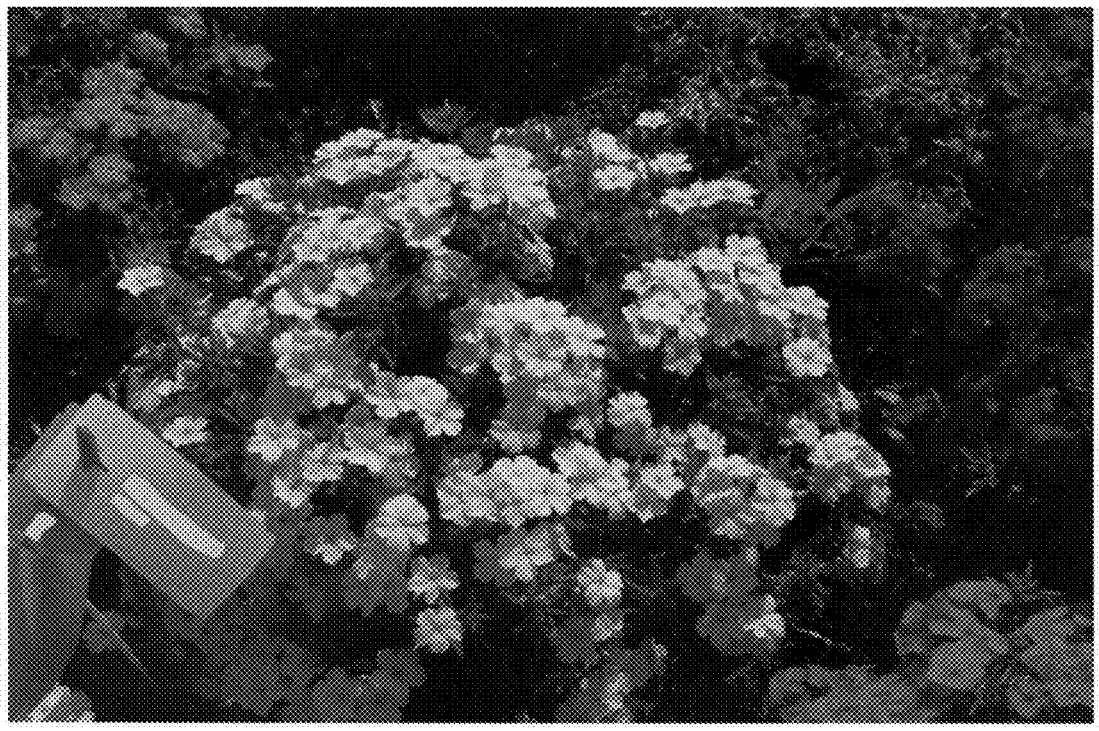

* * * * *